United States Patent [19]

Hein et al.

[11] Patent Number: 5,376,092
[45] Date of Patent: Dec. 27, 1994

[54] REAMER FOR SHAPING BONE SOCKETS

[75] Inventors: Todd J. Hein, Minneapolis; Mike K. Utley, Hopkins, both of Minn.

[73] Assignee: Orthopaedic Innovations, Inc., Minneapolis, Minn.

[21] Appl. No.: 154,703

[22] Filed: Nov. 18, 1993

[51] Int. Cl.⁵ .............................. A61B 17/16
[52] U.S. Cl. .............................. 606/81; 407/54; 408/227; 408/207
[58] Field of Search ............... 606/81; 407/53, 54, 407/60–63; 408/207, 227

[56] References Cited

U.S. PATENT DOCUMENTS

| | | | |
|---|---|---|---|
| 3,702,611 | 11/1972 | Fishbein . | |
| 4,131,116 | 12/1978 | Hedrick . | |
| 4,621,637 | 11/1986 | Fishbein . | |
| 4,811,632 | 3/1989 | Salyer | 76/101 |
| 5,100,267 | 3/1992 | Salyer | 407/54 |
| 5,116,165 | 5/1992 | Salyer | 407/54 |
| 5,203,653 | 4/1993 | Kudla | 408/207 |
| 5,290,315 | 3/1994 | DeCarlo, Jr. | 606/81 |

Primary Examiner—Tamara L. Graysay
Attorney, Agent, or Firm—Amy J. Hoffman; Jennifer K. Farrar

[57] ABSTRACT

A reamer for shaping a socket, such as a hip socket, comprising a cutting head located at one end of a rotatably driven shaft and having a hemispherical portion with a hemispherical exterior surface. The hemispherical portion containing an open substantially hollow chamber and helical openings such as slots, in said hemispherical portion connecting between the exterior surface and the chamber. The trailing portion of each of the openings having a cutting or trailing edge raised slightly above the leading edge of the opening or slot to move material from the socket into the chamber during rotation of the cutting head. The cutting edges having serrations thereon. At least two cutting edges extending across the polar region of the cutting head. A stem extending from the interior center point of the substantially hollow chamber and extending along the polar axis of the hemispherical reamer for connecting and disconnecting the cutting head to a rotatable source.

10 Claims, 4 Drawing Sheets

REAMER FOR SHAPING BONE SOCKETS

BACKGROUND OF THE INVENTION

The present invention relates to a reamer for shaping bone sockets which has improved cutting characteristics and improved attachment means. More specifically, the invention relates to a hemispherical reamer for shaping acetabulum.

DESCRIPTION OF THE PRIOR ART

Power driven reamers or bone cutters are utilized to round out and reshape the acetabular cavity or socket of the hip following the destruction of cartilage or bone at the hip socket. Such power driven bone cutters utilize a plurality of blades having the cutting edges protecting slightly above the hemispherical rotary head of the cutter. U.S. Pat. No. 3,633,583 discloses a substantially hemispherical head having a single surgical blade which provides two radially disposed cutting edges on opposite sides of the rotational center line of the head. The edges project slightly above the substantially hemispherical surface of the cutting head and the cutting edges are beveled in opposite directions on opposite sides of the axis of rotation so that both edges cut during rotation of the head. Troughs or grooves are formed in the head forward of the cutting edges to transport the cut bone from the surface of the head to the back of the head. U.S. Pat. No. 4,621,637 discloses a hollow acetabular reamer having three radial cutting blades. The blades have slots adjacent to the blades which allow debris to fall within the cup.

Another bone cutter having a hemispherical shaped cutting head is disclosed in U.S. Pat. No. 4,131,116. The '116 cutter has a plurality of radial cutter slots passing from the exterior surface of the cutting head into a hollow chamber within the head. At the trailing side of each slot is formed a cutting edge which projects slightly above the surface of the cutting head. Each cutter edge extends beyond the surface of the head and removes a small portion of bone or cartilage from the hip socket. This cut bone then passes through the slot forward of the cutting edge into the head chamber where it is retained until the head is removed from the drive shaft. Thus, this type of cutting head allows no loose bone or cartilage in the vicinity of the hip socket during rotation of the cutting head. By using at lease three slots and cutting edges, the head is equally loaded during rotation in all radial directions so that no tendency for tipping of the axis of rotation of the head exists as the cutting operation proceeds. The cutting edges and slots of the '116 cutting head are formed so that at least one slot and cutting edge passes over the point at which the end of the axis of rotation intersects the cutting head. This allows total removal of the complete surface of the hip socket. Both of the above-cited patents include only radial cutting edges and slots.

U.S. Pat. No. 5,203,653 discloses a hemispherical shaped cutting head with a plurality of helical cutter slots passing from the exterior surface of the cutting head into a hollow chamber within the head. The '653 cutter has only one cutting edge which extends over the center of the hemispherical shaped cutter. The '653 cutter discloses an attachment means which encloses the interior portion of the cutting head. Therefore, the cutting head fills with debris and must be removed and emptied before further cutting can proceed.

The present invention is an improved version of the cutting head of U.S. Pat. No. 5,203,653. The cutting head of the present invention has superior cutting ability by providing a reamer having two cutting edges which extend across the center of the hemispherical cutting head. Therefore, during rotation of the head, the present invention achieves more complete cutting than previous reamers. Due to the improved attachment means of the present reamer to a rotatable shaft, the reamer of the present invention does not fill with debris because the head is not entirely enclosed. Moreover, the attachment means provides for quick attachment and detachment of the reamer to a rotatable source. The present invention also includes serrated cutting blades which facilitate the removal of bone and cartilage. The use of helical shaded slots produces more efficient cutting in that the bone or tissue is sliced rather than scraped off as was the case with the radially slotted reamers.

SUMMARY OF THE INVENTION

It is an object of the present invention to provide a reamer for use in preparing acetabulum to receive a prosthetic implant which has efficient cutting characteristics and facilitates debris removal during cutting. It is a further object of the present invention to provide a hemispherically-shaped reamer having at least two cutting surfaces extending across the central external surface area of the cutting head. It is yet a further objective of the invention to provide a connecting means for connection to a rotating shaft which does not require the internal cavity of the cutting head to be sealed. This facilitates debris removal during cutting without requiring the surgeon to empty the cutting head during the operation.

Accordingly, these and other objects of the invention are provided by a reamer for shaping an acetabular socket which includes a hemispherical cutting head having a substantially hollow interior. The cutting head has at least two slots with grooves extending therefrom. More preferably, the cutting head has a plurality of slots with grooves extending therefrom. At least two of the grooves traverse the polar region of the hemispherical cutting head. The pole on the hemisphere is defined by the polar axis of the hemisphere. At least two cutting edges extend across this polar region to ensure complete cutting across the entire surface of the cutting head. Each slot has a trailing cutting edge having a radius from the center of the hemisphere greater than the radius to the leading edge of the slot. The slicing action of the helical slots and the hemispherical cutting head allows efficient cutting and removal of material. The severed tissue is moved into the substantially hollow interior or cavity of the cutter during rotation of the cutting head.

In the preferred embodiment, two sets of grooves which extend from four helical slots each converge to provide two cutting edges which traverse the center of the hemispherical cutting head. The present invention includes at least two helical slots spaced at 180°. Preferably, the invention includes six helical slots spaced at 60°. A critical feature of the invention includes two cutting edges which extend across the polar region of the hemispherical cutting head. In order to improve reaming efficiency, the exterior surface of the hemispherical cup in the area adjacent the trailing edge of each slot is relieved by removing material so that the area immediately trailing the cutting edge has a radius less than the radius of the trailing edge or the cutting edge of each slot. The trailing or cutting edge of each slot is serrated to facilitate tissue cutting.

The present invention further includes a stem which begins at the center of the interior surface of the hemispherical cutting head and extends along the polar axis of the hemisphere. This stem serves as a means to connect the reamer to a rotating shaft. Such an attachment allows the cavity in the cutting head to remain open. Therefore, the cutting head never fills with debris and does not require emptying during the cutting procedure. The stem attachment also provides a surgeon means to quickly and easily change reamer size during an operation. These and other objects and advantages of the present invention will become apparent from the following description of the accompanying drawings, which disclose one embodiment of the invention. It is to be understood that the drawings are to be used for purposes of illustration only, and not as a definition of the invention.

DETAILED DESCRIPTION OF THE INVENTION

Figure 1:
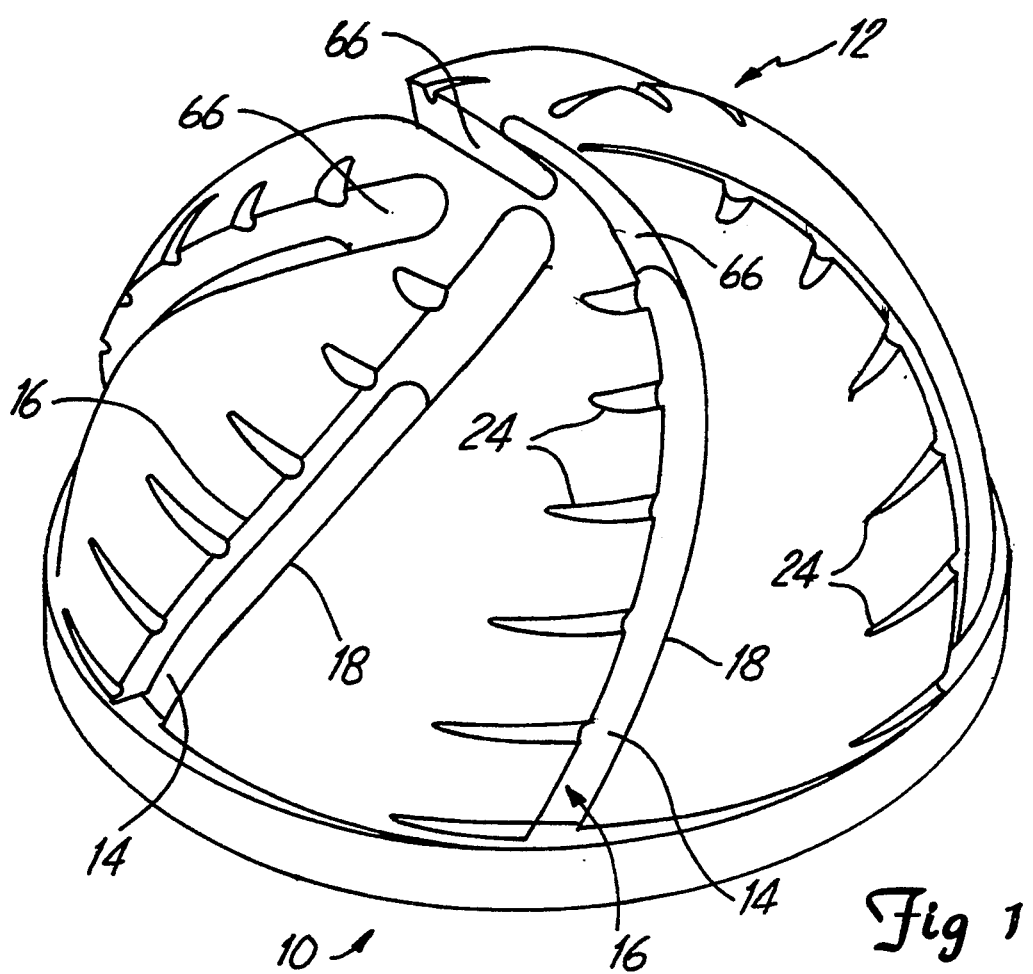
FIG. 1 is an isometric view of the hemispherical cutting head or reamer of the present invention including six helical slots formed therein.
Figure 2:
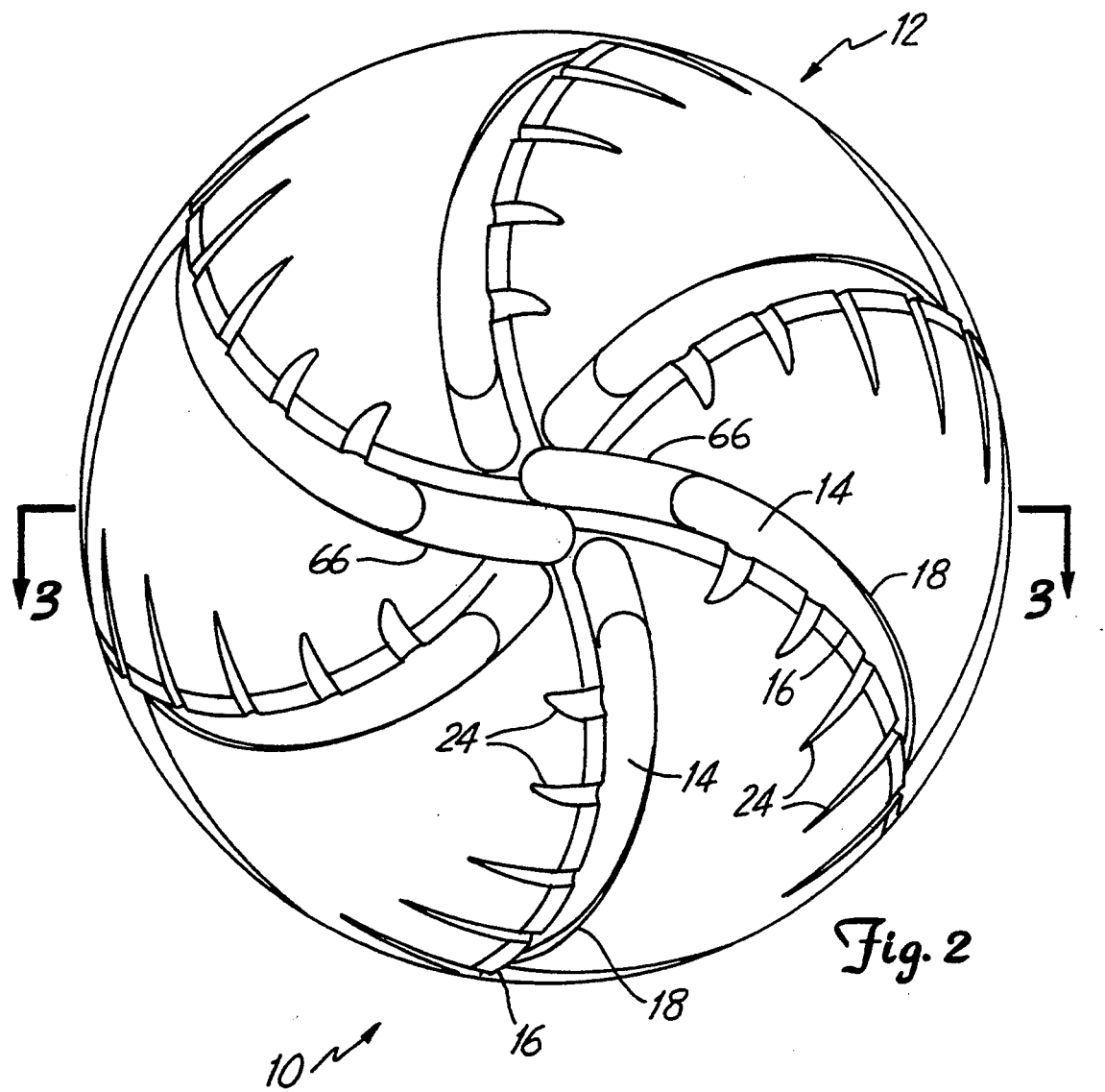
FIG. 2 is a plan view of the reamer as shown in FIG. 1.
Figure 3:
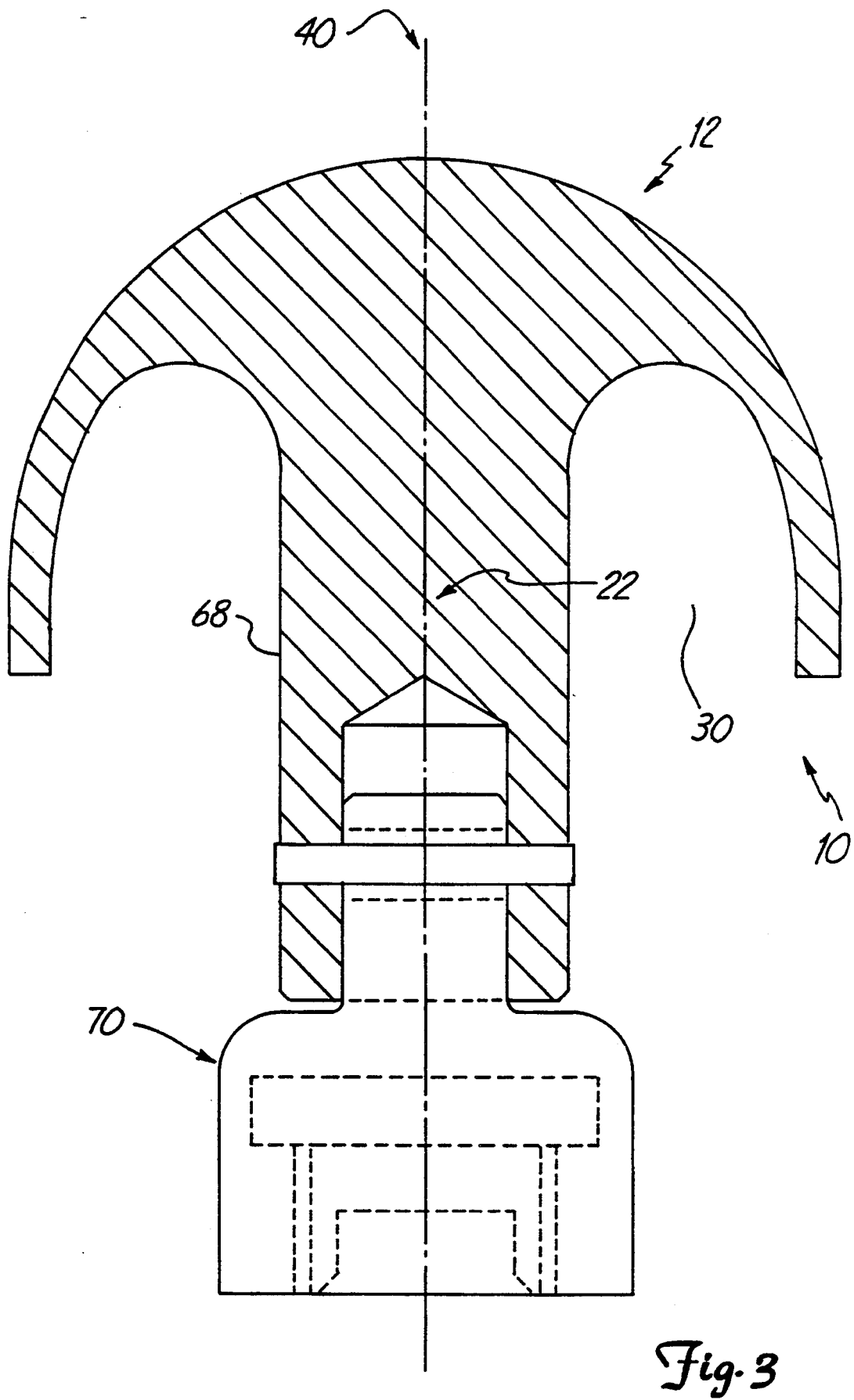
FIG. 3 is a cross sectional view taken along line 3—3.
Figure 4:
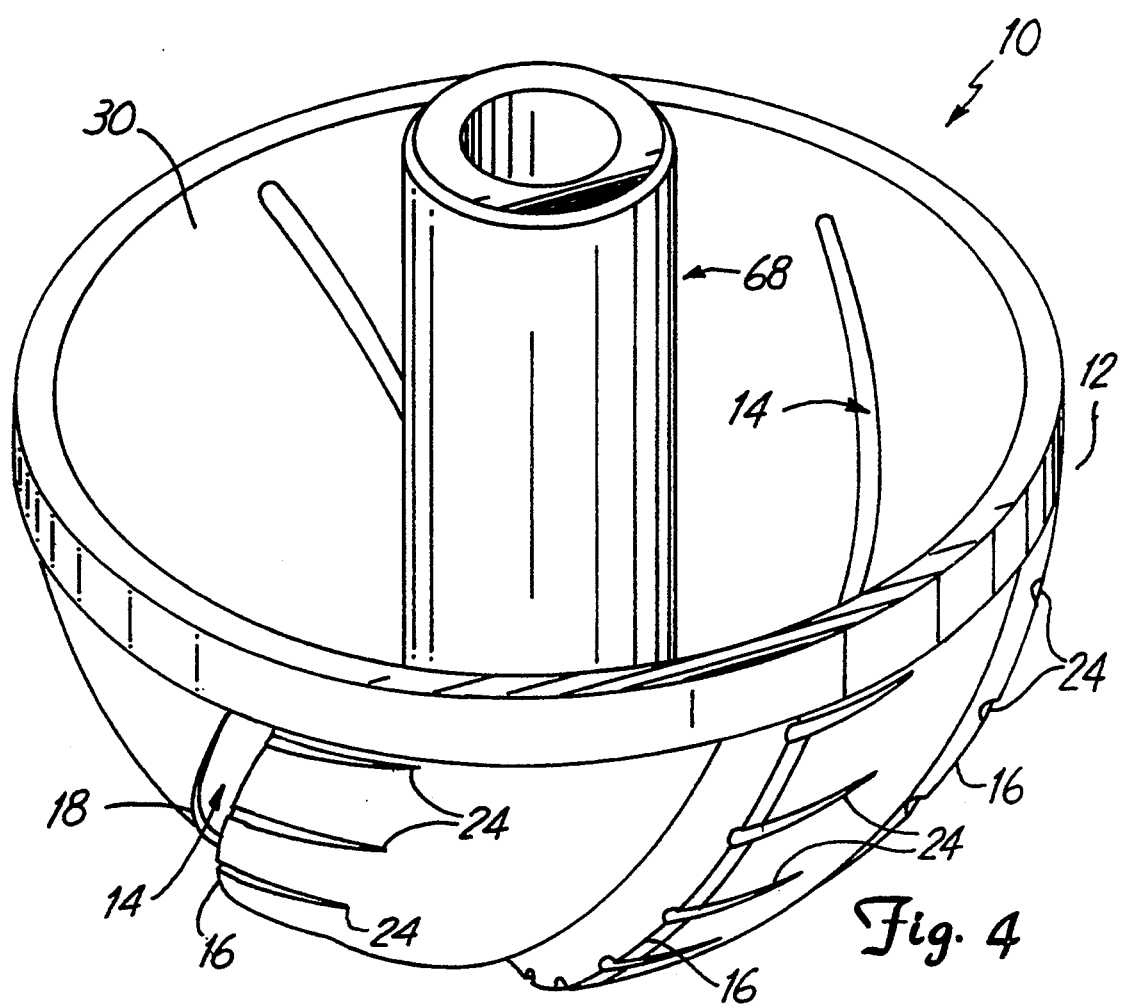
FIG. 4 is a bottom isometric view of the reamer of the present invention.

Referring to FIGS. 1-4 there is shown a reamer generally denoted as 10 for shaping a bone socket and in particular, an acetabular socket prior to implantation of a prosthetic acetabulum (not shown). The reamer is comprised of a substantially hollow hemispherical cutting head 12 containing a plurality of slots 14 with grooves 66 extending therefrom. In the preferred embodiment, there are six slots spaced at 60° around the circumference of the hemispherically-shaped cutting head 12. While six slots 14 are shown, two slots spaced at 180° are also effective. As best shown in FIGS. 1 and 4, each slot 14 includes a trailing edge 16 and a leading edge 18. Trailing edge 16 forms the cutting edge on the reamer 10. Trailing edge 16 extends at a radius R1 from center 22 of hemispherical cutting head 12. Radius R1 is greater than radius R2 which defines the distance the leading edge 18 of the outer surface of the cutting head 12 extends from the center 22. The radius of the leading edge 18 is preferably relieved by cutting off and by tilting the cutting head during fabrication so that the leading edge 18 is below cutting edge 16. As earlier described, this facilitates cutting and debris removal into the hollow chamber 30 of the cutting head 10.

In the preferred embodiment, the trailing edge 16 is serrated with serrations 24 to allow for more efficient cutting of the cartilage or bone. In the preferred embodiment, if serrations 24 are connected they form a helix which spirals down the hemispherical surface of the cutting head 12 from the polar region. The serrations aid in cutting and also help to sweep the debris through the slots 14 and into the hollow chamber 30.

Referring to FIGS. 3 and 4 showing a cross sectional view and an isometric bottom view of the cutting head 12. The substantially hollow interior portion or cavity 30 includes a central stem 68. The stem 68 extends from the center of the hollow hemispherical cavity along the polar axis 40 of the hemisphere. The stem 68 provides a desirable means for attaching the reamer 10 to a rotatable shaft 70. A rotating shaft 70 is attached to the stem 68 by any means commonly known in the art. The stem 68 attachment provides a quick and easy means of attaching and detaching the reamer 10 from a rotatable source 70. This allows a surgeon to quickly size the bone and detach and change the reamer 10 if a larger or smaller cavity is desired. Although a stem attachment is preferred, other means of attachment such as a lure lock is also possible for attaching the reamer 10 to a rotatable shaft 70.

The present reamer 10 is fitted on a rotational drive shaft 70 allowing rotation of the reamer. Due to the helical cut slots 14, debris is drawn to the interior of the cutting head. Since the reamer cavity 30 is substantially hollow and is never sealed, the cutting head 12 never fills with debris. Thus, the present invention provides a reamer 10 having an extended period of use as compared to a reamer which is substantially sealed.

Reamer 10 may be supplied in various sizes. For example, reamer 10 may range from 26 millimeters in diameter to 70 millimeters in diameter, all having at least 2 slots 14 therein. Slot sizes 14 vary in size depending upon the overall size of the reamer. For example, a 26 millimeter reamer will have a much smaller slot width than a 50 millimeter reamer. The 26 millimeter reamer may include slots having widths less than 1 millimeter while a 50 millimeter reamer may have slots exceeding 4 millimeters in width.

Due to the stem location 68, the present invention is afforded the ability to include two cutting edges 16 which traverse the polar region of the cutting head 12. The stem 68 provides a thicker portion directly behind the polar axis of the hemispherical cutting head 12. Because of the thickened region, grooves 66 are able to traverse the center point of the cutting head. Alternatively, two or more grooves 66 may converge without affecting the integrity of the reamer 10. Grooves 66 extend from slots 14. The slots 14 converge towards the center of the hemispherical cutting head 12 and two grooves 66 actually traverse the center point. In the preferred embodiment, two sets of grooves 66 converge near the polar axis to form two cutting edges 16 which traverse the center of the cutting head 12. Two cutting edges 16 which traverse the center, coupled with the serrated trailing or cutting edges 16 provide increased cutting ability.

While several examples of the present invention have been described, it is obvious that many changes and modifications may be made without departing from the spirit and scope of the invention.

We claim:
1. A reamer for shaping a socket comprising:
   a cutting head comprising a hemispherical portion having a hemispherical exterior surface and containing a substantially hollow chamber;
   at least two elongate helical slots each extending along a single plane between said hemispherical exterior surface and said chamber wherein the slots move toward converging near the center point of said hemispherical exterior surface but never converge;
   a cutting edge on the trailing portion of each of said slots;
   a leading portion opposite said trailing portion on each of said slots and relieved slightly below said hemispherical exterior surface of said hemispherical portion for moving material from said socket into said chamber during the rotation of said reamer; and grooves extending from said slots wherein at least two of said grooves traverse the center point of said hemispherical exterior portion to form at least two cutting edges which traverse the center portion of said hemispherical exterior surface.

2. The reamer as set forth in claim 1 wherein said cutting edge is serrated.

3. The reamer as set forth in claim 2 wherein said serrations helically spiral from the center of said hemispherical exterior surface.

4. The reamer as set forth in claim 1 wherein said slots are six in number and are spaced 60° around the exterior surface of said cutting head.

5. The reamer as set forth in claim 1 further comprising a stem connected to the interior surface of said substantially hollow chamber at the center of said interior surface and extending along the polar axis.

6. A reamer for shaping a socket comprising:

a cutting head comprising a hemispherical portion having a hemispherical exterior surface and containing a substantially hollow chamber;

a stem connected to the interior surface of said substantially hollow chamber at the center of said interior surface and extending along the polar axis, said stem suited for detachably connecting said reamer to a rotatable source;

at least two elongate helical slots each extending along a single plane between said hemispherical exterior surface and said chamber wherein the slots move toward converging near the center point of said hemispherical exterior surface but never converge;

a cutting edge on the trailing portion of each of said slots;

a leading portion opposite said trailing portion on each of said slots and relieved slightly below said hemispherical exterior surface of said hemispherical portion for moving material from said socket into said chamber during the rotation of said reamer; and grooves extending from said slots wherein at least two of said grooves converge near the center point of said hemispherical exterior portion to form at least two cutting edges which traverse the center portion of said hemispherical exterior surface.

7. The reamer as set forth in claim 6 wherein said cutting edge is serrated.

8. The reamer as set forth in claim 7 wherein said serrations helically spiral from the center of said hemispherical exterior surface.

9. The reamer as set forth in claim 6 wherein said slots are six in number and are spaced 60° around the exterior surface of said cutting head.

10. The reamer of claim 6 wherein two sets of grooves converge near the center point of said hemispherical exterior surface.

* * * * *